US00PP16401P3

(12) United States Plant Patent
Glenn

(10) Patent No.: US PP16,401 P3
(45) Date of Patent: Apr. 4, 2006

(54) OAK TREE NAMED 'QNSTC'

(50) Latin Name: *Quercus* sp.
Varietal Denomination: QNSTC

(75) Inventor: Michael M. Glenn, Bogart, GA (US)

(73) Assignee: Tree Introductions, Inc., Bishop, GA (US)

( * ) Notice: Subject to any disclaimer, the term of this patent is extended or adjusted under 35 U.S.C. 154(b) by 120 days.

(21) Appl. No.: 10/823,472

(22) Filed: Apr. 12, 2004

(65) Prior Publication Data

US 2005/0229280 P1 Oct. 13, 2005

(51) Int. Cl.
*A01H 5/00* (2006.01)

(52) U.S. Cl. ..... Plt./225

(58) Field of Classification Search ..... Plt./225
See application file for complete search history.

(56) References Cited

PUBLICATIONS

Preston, R. J. North American Trees, 1950. The Iowa State College Press, p. 199.*
The New Royal Horticultural Society Dictionary of Gardening, 1992, p. 786.*

* cited by examiner

*Primary Examiner*—Anne Marie Grunberg
*Assistant Examiner*—June Hwu
(74) *Attorney, Agent, or Firm*—Klarquist Sparkman, LLP

(57) ABSTRACT

An Oak tree named 'QNSTC' having a dense, upright branching habit and consistent red to orange fall color, and also capable of being reproduced reliably using vegetative cuttings.

7 Drawing Sheets

Latin name of genus and species: *Quercus* sp.
Variety denomination: 'QNSTC'.

BACKGROUND OF THE INVENTION

The present invention relates to a new and distinct variety of *Quercus nuttallii,* which has been given the varietal name 'QNSTC'. I discovered my new tree in 2001 as a chance seedling in a cultivated area of a nursery in Oconee County, Ga. This cultivated area also contained other seedling oak trees. The new variety differed from these other seedling oak trees growing in this area by its dense, upright branching habit and consistent red fall color.

The parentage of this tree is unclear. It is definitely a red oak type tree. Representative species include Pin Oak (*Q. palustris*), or Red Oak (*Q. rubra*). There are also several related species, including Nuttall Oak (*Q. nuttallii*), Shumard Oak (*Q. shumardii*), and Scarlet Oak (*Q. coccinea*). My new tree has characteristics and a history that have prevented making an exact identification of its species, but Nuttall Oak appears to be the closest.

Nuttall Oak, as well as most other red oak types, readily hybridize with one another, and there is a high probability that this tree is a result of a cross between a Nuttall Oak and Shumard Oak or some other species of red oak, since Nuttall Oak and Shumard Oak overlap one another across much of their range. For example, in Texas, Nuttall is found in the lower Southeast corner of the state, Shumard is located in a wide band covering most of the eastern part of the state, and Texas Red Oak (*Q. texana*), is the primary tree in the central part of the state east of Dallas. There is also a large swath of habitat between the primary Shumard and Texas Red Oak regions where the predominant tree is a hybrid between Shumard and Texas Red Oak. Hybrids are common and can easily make up a large population of the trees in any given area.

My original tree had been purchased as a 12 to 18 inch liner in spring 1996 and at that time planted in a liner field. All of the purchased liners were grown from seeds. This tree was transplanted to another field in spring 1998 and subsequently discovered by me. In December 2003, it was transplanted to an observation area where it has remained since that time. It is now 9 years old from a seed. The description of this new Oak variety is based on observations of this original tree and of asexually propagated progeny, produced from vegetative propagation that are being grown at a nursery in Oconee County, Ga.

The original tree has displayed characteristics resembling Nuttall Oak and Shumard Oak. There is much confusion over the exact identification of this tree, and several experienced individuals have expressed differing opinions. The only consistency has been the opinion that the acorn is generally the most distinguishig characteristic determining the species difference between Nuttall Oak and Shumard Oak. When compared to the above oaks, the acorns on my new tree most resemble Nuttall Oak, which indicates that the tree is most likely a Nuttall Oak or at least has Nuttall Oak as one of its parents. Other physical characteristics of the tree, such as leaf size, sinus depth, or bud features, do not provide definitive answers as to the true parentage of the tree.

BRIEF SUMMARY OF THE INVENTION

As I observed the original tree of my new variety, the uniqueness of this tree became apparent because of its dense, upright branching habit and consistent red to orange fall color. These characteristics distinguish my new tree from other Nuttall Oaks of which I am aware.

My new variety was asexually propagated by softwood cuttings in 2001 at my direction, in Oconee County, Ga. The progeny have thus far proven to retain the dense, upright branching habit and consistent red to orange fall color of the original tree, even as smaller plants. This propagation and observation of the resulting progeny have proven the characteristics of my new variety to be firmly fixed and reproduce true to type. Furthermore, these observations have confirmed that my new variety represents a new and improved variety of oak tree, which appears to be a variation of Nuttall Oak trees based upon observations of acorns in the original tree and as particularly evidenced by the dense, upright branching pattern and consistent red to orange fall color, and which can reliably be asexually propagated using vegetative propagation.

I observed this tree of my new variety for a period of time and believe it is particularly useful as a specimen or for groupings in lawns, parks, golf courses, commercial landscapes, and as a street tree. It provides good shade, is a relatively fast growing tree, and has good structural branching. It also provides ornamental insterest with its consistent red to orange fall color.

Cultivated Nuttall Oak is represented in the industry mostly by seedling material. Seedling material has a wide range of variability, and as is illustrated by information in this patent, there may be uncertainty as to the trueness of type from the seed. My new tree has a dense, upright branching habit and consistent red to orange fall color not represented consistently by any other Nuttall Oak tree cultivar known to me. 'QNFTA' (U.S. Pat. No. 13,524) is a Nuttall cultivar that has an upright-pyramidal branching habit, but has more orange fall foliage then my new tree and some yellow fall foliage that my new tree does not have. In addition, in comparing the overall habit of my new tree to 'QNFTA', my new tree has a denser branching canopy than 'QNFTA.'

Typical Nuttall and Shumard are pyramidal trees that become more spreading with age. My tree has a dense, upright shape, but I expect it to become more spreading with age as is typical of the species. My new tree has a full, dense canopy and a central leader that is more typical of a Nuttall Oak tree. Both Nuttall Oak and Shumard Oak typically reach 40 to 60 feet high and wide in the landscape, but can reach 100 feet or more in nature. The ultimate height and width of my new variety is not known.

BRIEF DESCRIPTION OF THE DRAWINGS

The accompanying photographs depict the color of the tree and foliage of my new variety as nearly true as is reasonably possible to make the same in a color illustration of this character.

DETAILED BOTANICAL DESCRIPTION

My 'QNSTC' variety of Oak tree is currently growing at an observation site in Oconee County, Ga. It is located in an area of Oconee that has a clay loam soil type and receives approximately 50 inches of rain per year. Oconee County, Ga. is in USDA Hardiness Zone 7. Both Nuttall and Shumard are typically hardy in USDA Zones 5 through 9.

My new tree has not been observed under all growing conditions, and thus, variations may occur as a result of different growing conditions. The following is a detailed description of my new variety of my new tree with color terminology in accordance with The Royal Horticultural Society (R.H.S.) Colour Chart published by The Royal Horticultural Society in London. The observations are of the original tree growing at the observation site in Oconee County, Ga.

Parentage: Discovered as a change seedling of unknown origin growing in a cultivated area of a nursery in Oconee County, Ga. The parentage of this tree is believed to include Nuttall Oak, but is not entirely clear for reasons explained above.

Figure 1:
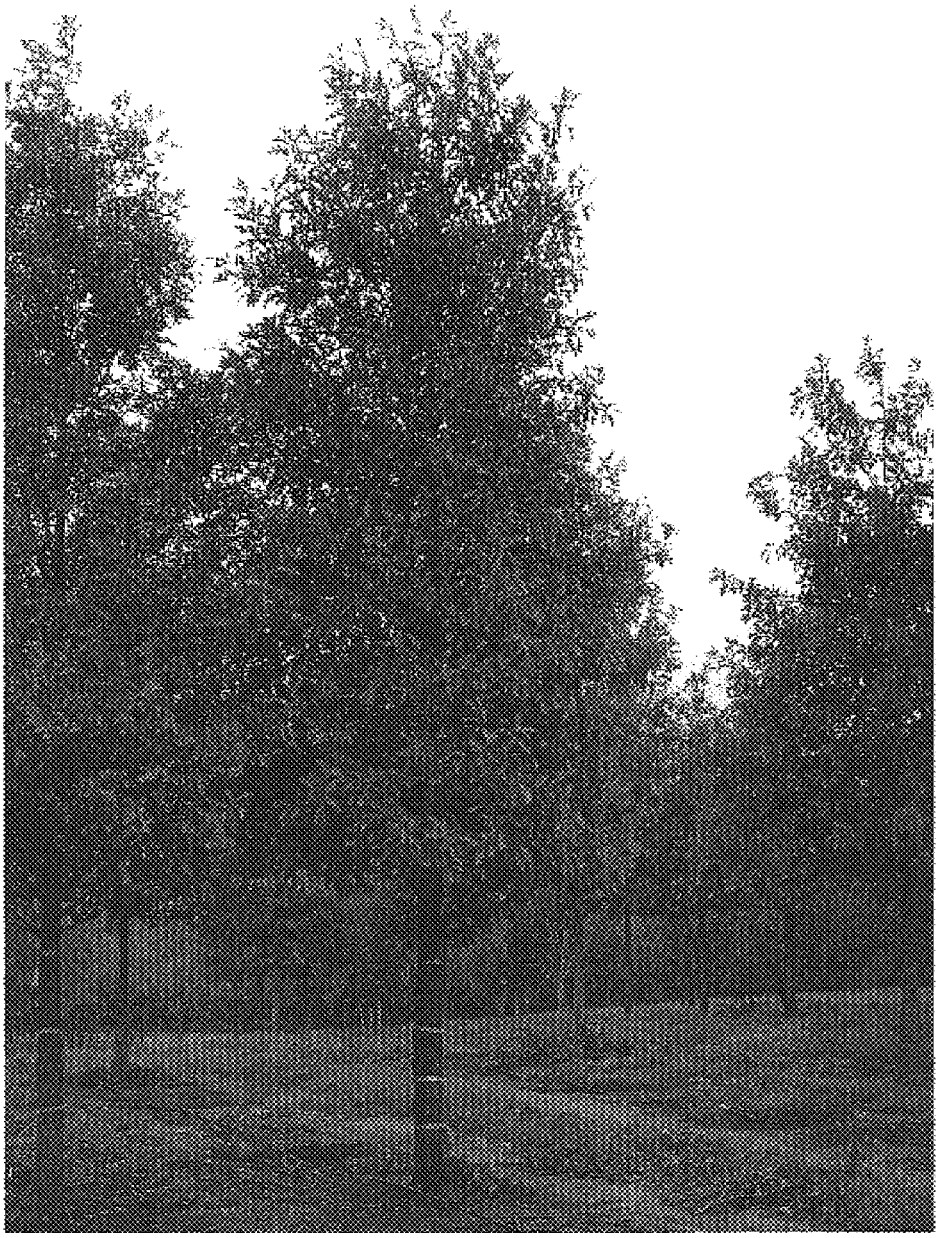
FIG. 1 is a photograph of the original tree of my new variety in summer leaf.
Figure 2:
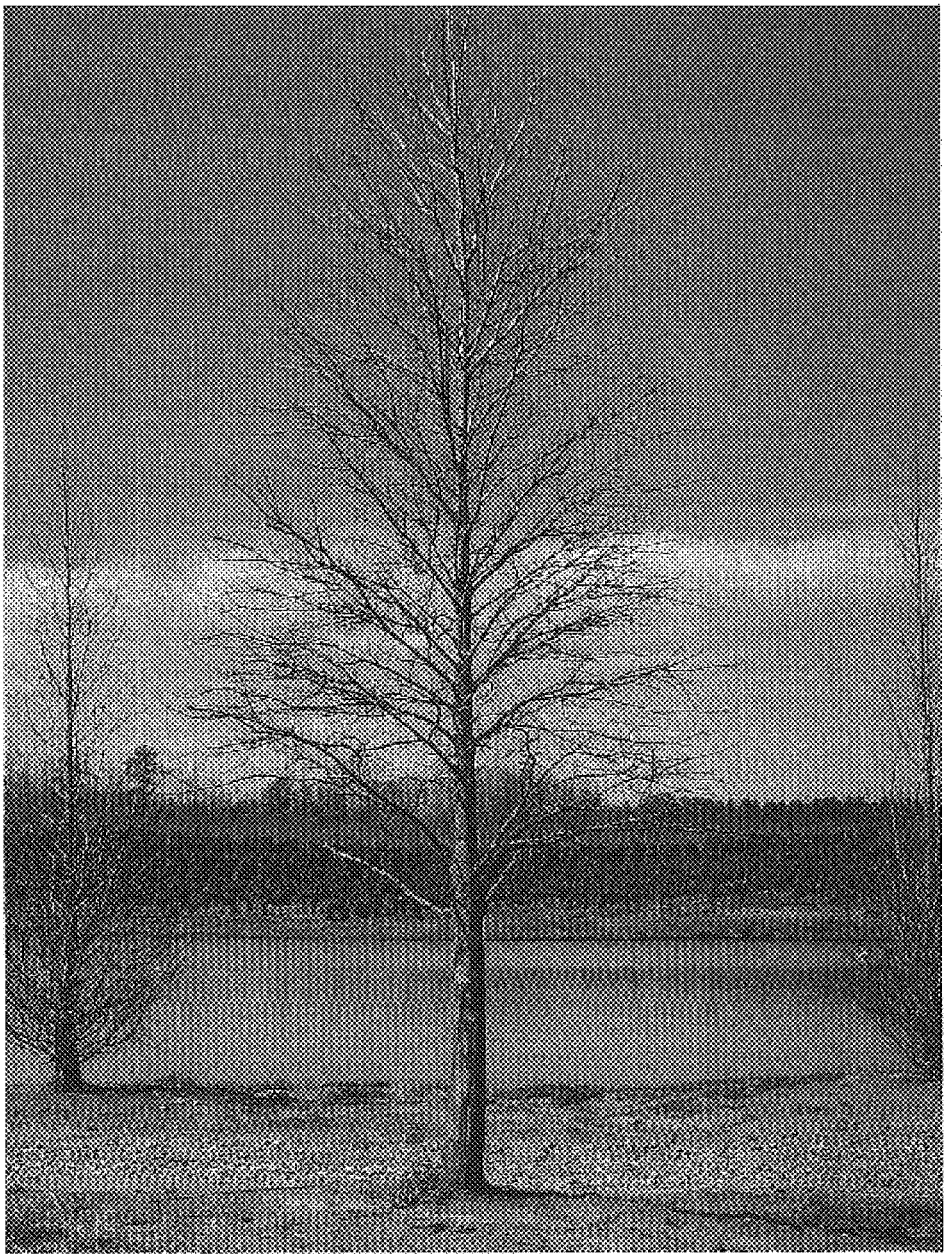
FIG. 2 is a photograph of the original tree of my new variety during winter.

Tree shape: Dense, upright canopy, with a central leader (FIGS. 1 and 2).

Trunk: The trunk is typical of the species with a strong central leader (bole). At about age ten, the initially discovered tree had a diameter of about six inches in diameter measured twelve inches above the ground.

Figure 6:
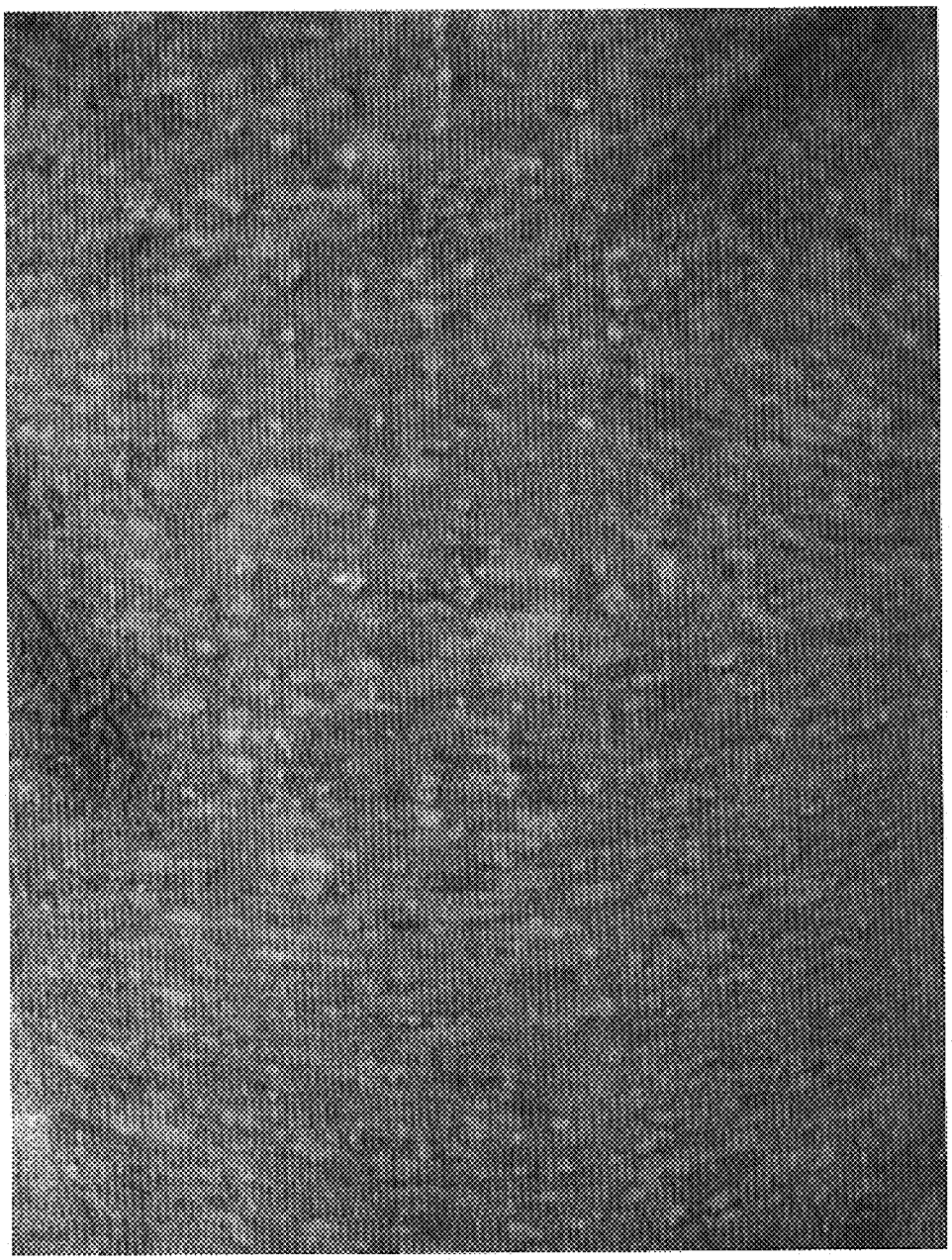
FIG. 6 is a close up of a typical section of the trunk of the original tree of the new variety.

Bark: Bark is typical of the species (FIG. 6), being smooth and gray (RHS 195B) with patches of light gray (RHS 156B) on young trees, with age, becoming roughened by shallow ridges and furrows. Mature bark is darker gray (RHS 198A) with patches of light gray (RHS 156B), also typical of the species.

Size and growth rate: The original tree is currently 8.1 inches in caliper at 12 inches above the ground, about 24 feet high, and about 11 feet wide, thus providing an overall height to width ratio of about 2.2. Prior to tranplanting to the observation site, the original tree had an average growth in caliper of about 1.35 inches per year. Root development from time of sticking is approximately six to eight weeks.

Figure 7:
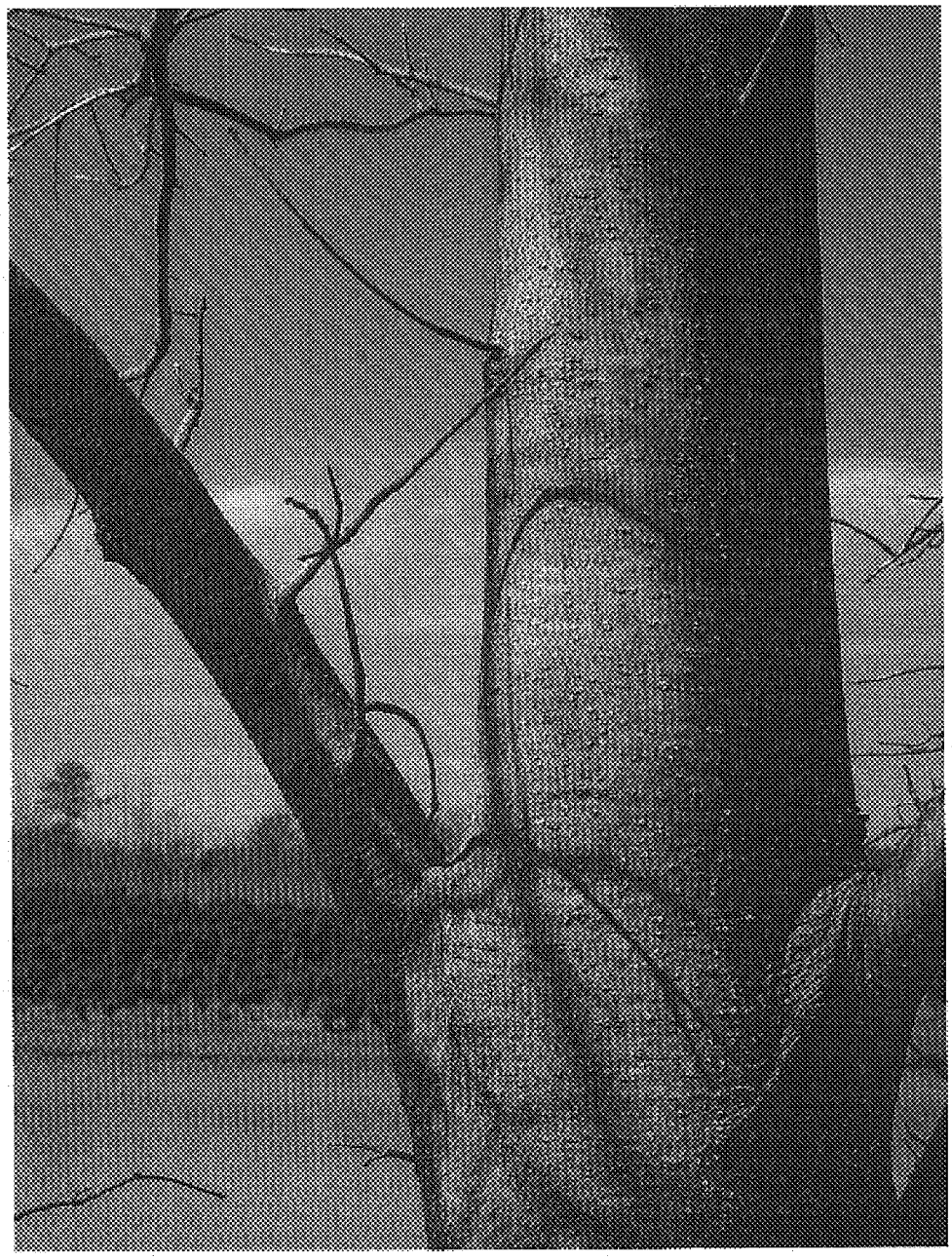
FIG. 7 is a close up of the branching angle of the original tree of the new variety.

Branching habit: Branching is somewhat more upright compared to most other seedling Nuttall Oaks. Primary branches emerge from the trunk at about a 45 degree angle to the leader (FIG. 7). We expect with age the angle to increase with respect to the leader.

*Branches.*—Surface texture is smooth. Color is gray-green (RHS 194B).

*Branch lenticels.*—On a branch having a 1½" caliper, average size is 1/16". Shape is round to oblong. Color is slight green-white (RHS 157C) to grey-white (RHS 156B).

Figure 3:
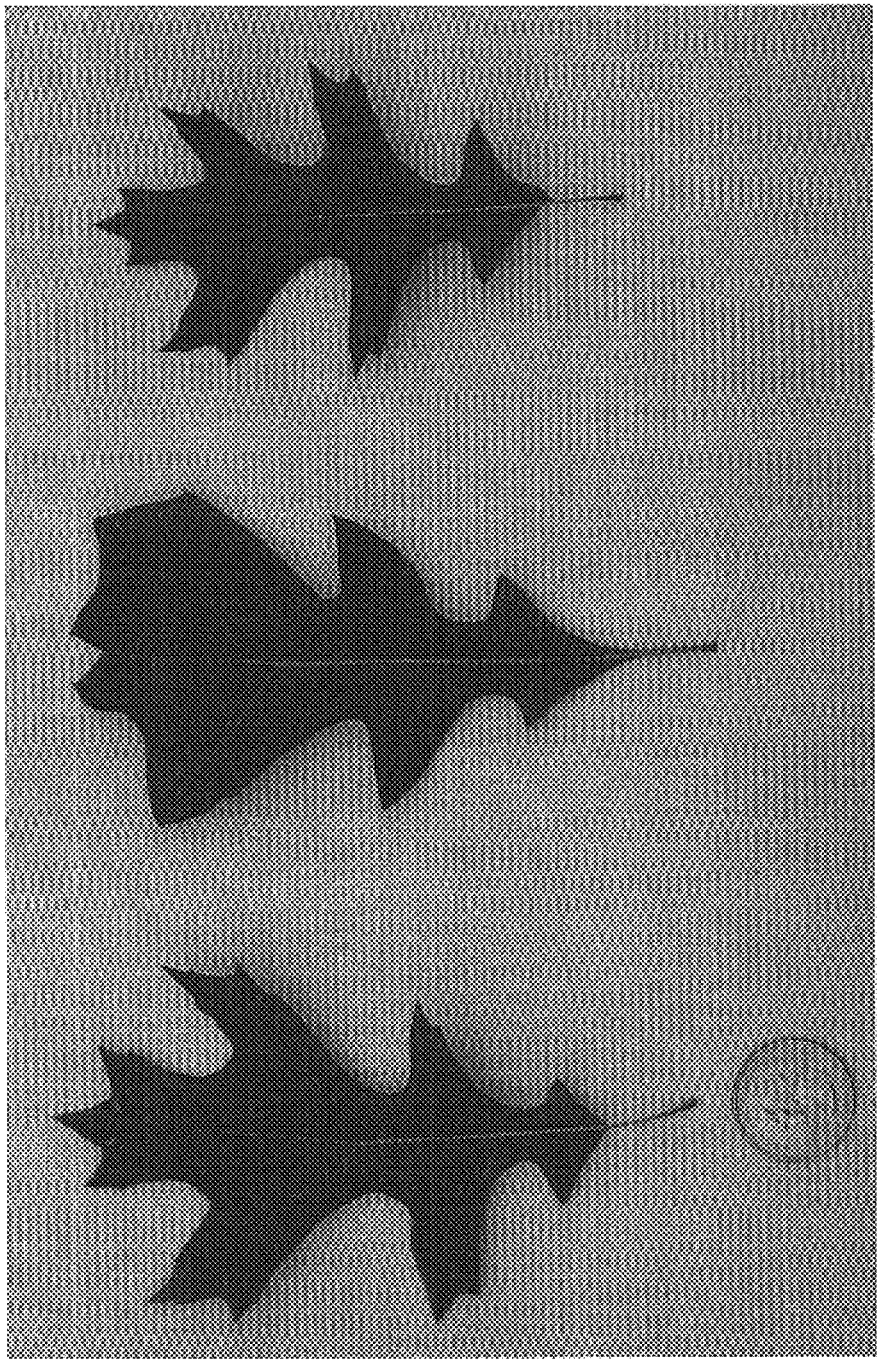
FIG. 3 is a close up of three single leaves depicting the upper side of leaves from a tree of my new variety. The US Quarter Dollar in the picture provides a sizing reference.
Figure 4:
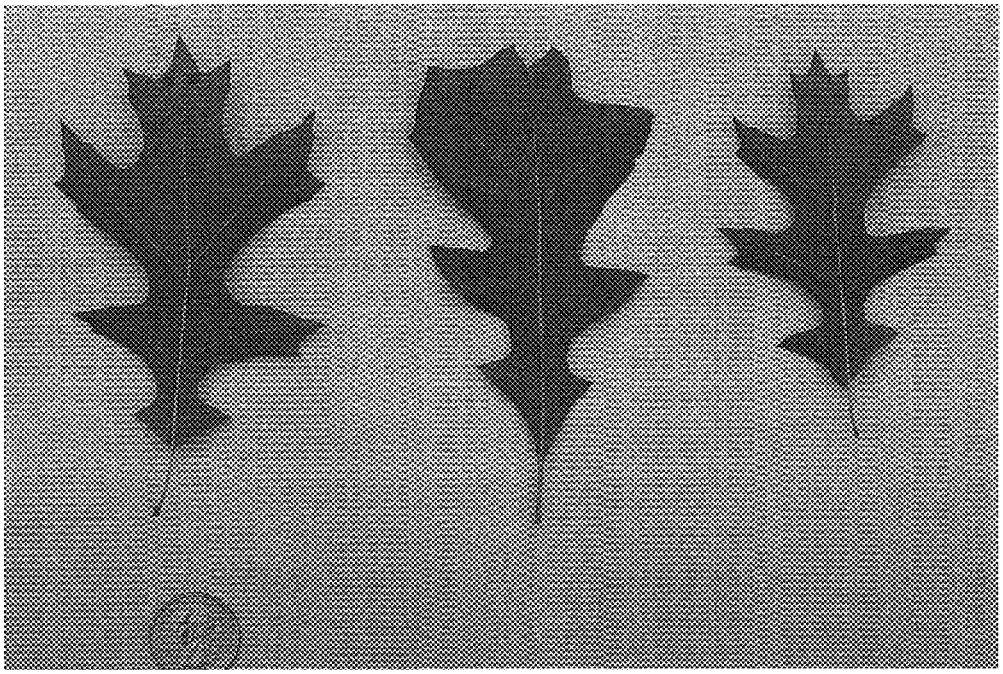
FIG. 4 is a close up of three single leaves depicting the under side of leaves from a tree of my new variety.
Figure 5:
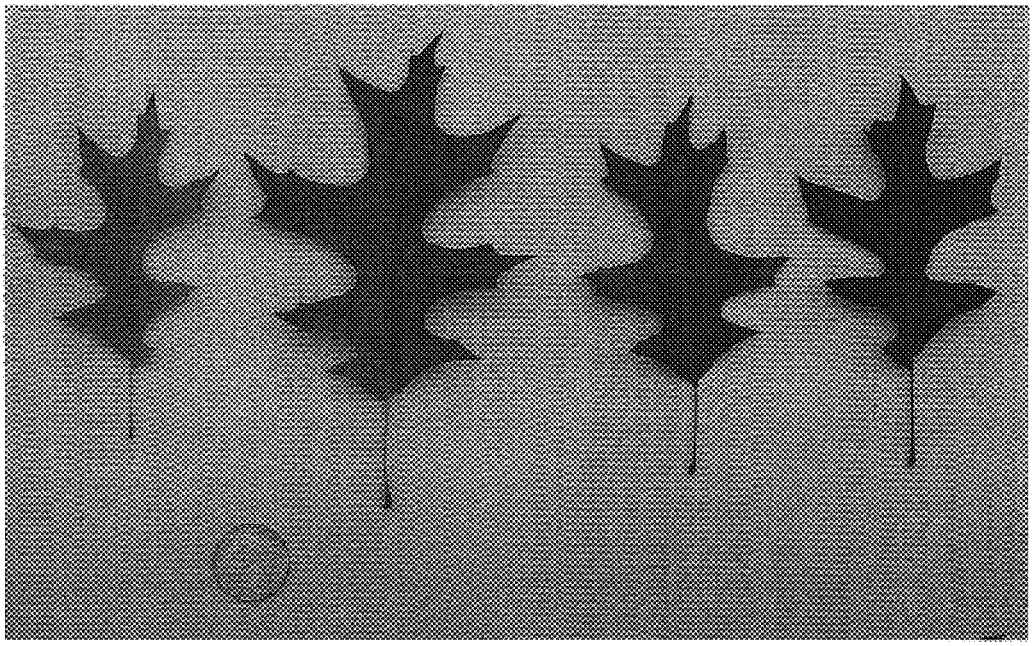
FIG. 5 is a close up of four leaves depicting fall leaf color of my new variety.

Foliage: The leaves of Nuttall, Shumard, and Pin all resemble one another, and my tree has leaves that are typical of *Q. nuttallii* in size and shape: Alternate, simple, obovate to elliptic, 4 to 9" long, 2 to 5" wide, with 5 to 9 lobes. Sinuses are round with narrow lobes. The leaves maintain a dark green color in summer (FIG. 3) (RHS 136B), and the lower leaf surface (FIG. 4) is a lighter green (RHS 138A). Consistent fall color (FIG. 5) which ranges from dark red (RHS 43A) to red orange (RHS 34B). Tufts of hairs are present on the underside vein axils.

*Overall shape.*—Lobed.

*Base.*—Pointed, less so than apex.

*Apex.*—Sharply pointed.

*Surface texture.*—Smooth, glaucous.

*Petiole.*—Average length approximately ⅜" to ½". Surface texture is smooth (glabrous). Color is dull green (RHS 153A).

Buds: Typical of the species, being imbricate, ⅛ to ¼" long, ash-gray (RHS 201A) to brown-gray (RHS 199B), and pubescent with ciliate scale margins.

Flowers: Typical of the species. However, most oaks have flowers so similar that it is difficult to distinguish between species based on flower type alone. The trees are monoecious. The staminate catkins are pendent and clustered. The individual flowers comprise a 4- to 7-lobed calyx that encloses 6 to 12 stamens. Pistillate flowers are solitary or in few to many-flowered spikes from the axils of the new leaves. Individual pistillate flowers consist of a 6-lobed calyx surrounding the ovary, with the whole partly enclosed in an involucre.

Fruit: Acorns are typical of species. Acorns are ovate, ¾ to 1¼41 long, short-stalked, oblong-ovoid, and covered ⅓ to ½ by the cap. The acorn is gray-orange in color (RHS 165A) with dark brown (RHS 200B) striations. The cap is light brown (RHS 199C).

Root system: The root system is typical of the species being fibrous.

Pest and disease resistance: My new tree variety appears to be typical of the species.

Winter hardiness: Not yet determined, due to only being grown and observed in Oconee County, Ga. (USDA Zone 7).

I claim:

1. A new and distinct variety of Oak tree substantially as herein shown and described, characterized particularly as to novelty by its dense, upright branching habit and its consistent red to orange fall color.

* * * * *

UNITED STATES PATENT AND TRADEMARK OFFICE

CERTIFICATE OF CORRECTION

PATENT NO. : PP 16,401 P3
APPLICATION NO. : 10/823472
DATED : April 4, 2006
INVENTOR(S) : Michael M. Glenn It is certified that error appears in the above-identified patent and that said Letters Patent is hereby corrected as shown below:

In the Specification:

Column 6, line 4, "1¼41" should be 1¼.

Signed and Sealed this

Fifteenth Day of August, 2006

JON W. DUDAS
*Director of the United States Patent and Trademark Office*